United States Patent
Forsberg

(10) Patent No.: US 8,007,514 B2
(45) Date of Patent: Aug. 30, 2011

(54) AUTOMATIC SUTURE LOCKING DEVICE

(75) Inventor: Andrew Thomas Forsberg, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1546 days.

(21) Appl. No.: 10/688,365

(22) Filed: Oct. 17, 2003

(65) Prior Publication Data

US 2005/0085855 A1    Apr. 21, 2005

(51) Int. Cl.
*A61B 17/04* (2006.01)
*A61B 17/08* (2006.01)

(52) U.S. Cl. .................. 606/232; 606/213

(58) Field of Classification Search .......... 606/213, 606/232, 151; 24/115, 129 R, 135 N
See application file for complete search history.

(56) References Cited

U.S. PATENT DOCUMENTS

| | | | |
|---|---|---|---|
| 4,890,612 A | 1/1990 | Kensey | 606/213 |
| 5,242,456 A | 9/1993 | Nash et al. | 606/142 |
| 5,405,354 A | 4/1995 | Sarrett | 606/148 |
| 5,411,520 A | 5/1995 | Nash et al. | 606/213 |
| 5,417,699 A | 5/1995 | Klein et al. | 606/144 |
| 5,476,469 A | 12/1995 | Hathaway et al. | 606/144 |
| 5,527,322 A | 6/1996 | Klein et al. | 606/144 |
| 5,549,633 A * | 8/1996 | Evans et al. | 606/139 |
| 5,613,974 A | 3/1997 | Andreas et al. | 606/144 |
| 5,645,566 A | 7/1997 | Brenneman et al. | 606/213 |
| 5,662,681 A | 9/1997 | Nash et al. | 606/213 |
| 5,681,334 A | 10/1997 | Evans et al. | 606/148 |
| 5,702,397 A * | 12/1997 | Goble et al. | 606/72 |
| 5,766,183 A | 6/1998 | Sauer | 606/139 |
| 5,782,861 A | 7/1998 | Cragg et al. | 606/216 |
| 5,792,152 A | 8/1998 | Klein | 606/144 |
| 5,860,990 A | 1/1999 | Nobles | 606/144 |
| 5,916,236 A | 6/1999 | Van de Moer et al. | 606/213 |
| 5,984,950 A | 11/1999 | Cragg et al. | 606/216 |
| 6,045,497 A * | 4/2000 | Schweich et al. | 600/16 |
| 6,071,300 A | 6/2000 | Brenneman et al. | 606/23 |
| 6,110,184 A | 8/2000 | Weadock | 606/144 |
| 6,132,439 A | 10/2000 | Kontos | 606/139 |
| 6,159,234 A * | 12/2000 | Bonutti et al. | 606/232 |
| 6,171,317 B1 | 1/2001 | Jackson et al. | 606/148 |
| 6,179,863 B1 | 1/2001 | Kensey et al. | 606/215 |
| 6,190,400 B1 | 2/2001 | Van De Moer et al. | 606/213 |
| 6,293,961 B2 * | 9/2001 | Schwartz et al. | 606/232 |
| 6,475,230 B1 * | 11/2002 | Bonutti et al. | 606/232 |
| 2003/0167062 A1 * | 9/2003 | Gambale et al. | 606/138 |
| 2004/0147958 A1 * | 7/2004 | Lam et al. | 606/232 |

* cited by examiner

*Primary Examiner* — Darwin P Erezo
*Assistant Examiner* — Jing Rui Ou
(74) *Attorney, Agent, or Firm* — Holland & Hart

(57) ABSTRACT

The present invention involves an automatic suture locking device useable with vascular closure device. The suture locking device includes a housing and a locking mechanism. The locking mechanism has locked and unlocked positions. In the locked position, a suture pathway through the mechanism is sufficiently tortuous to prevent free suture movement.

14 Claims, 6 Drawing Sheets

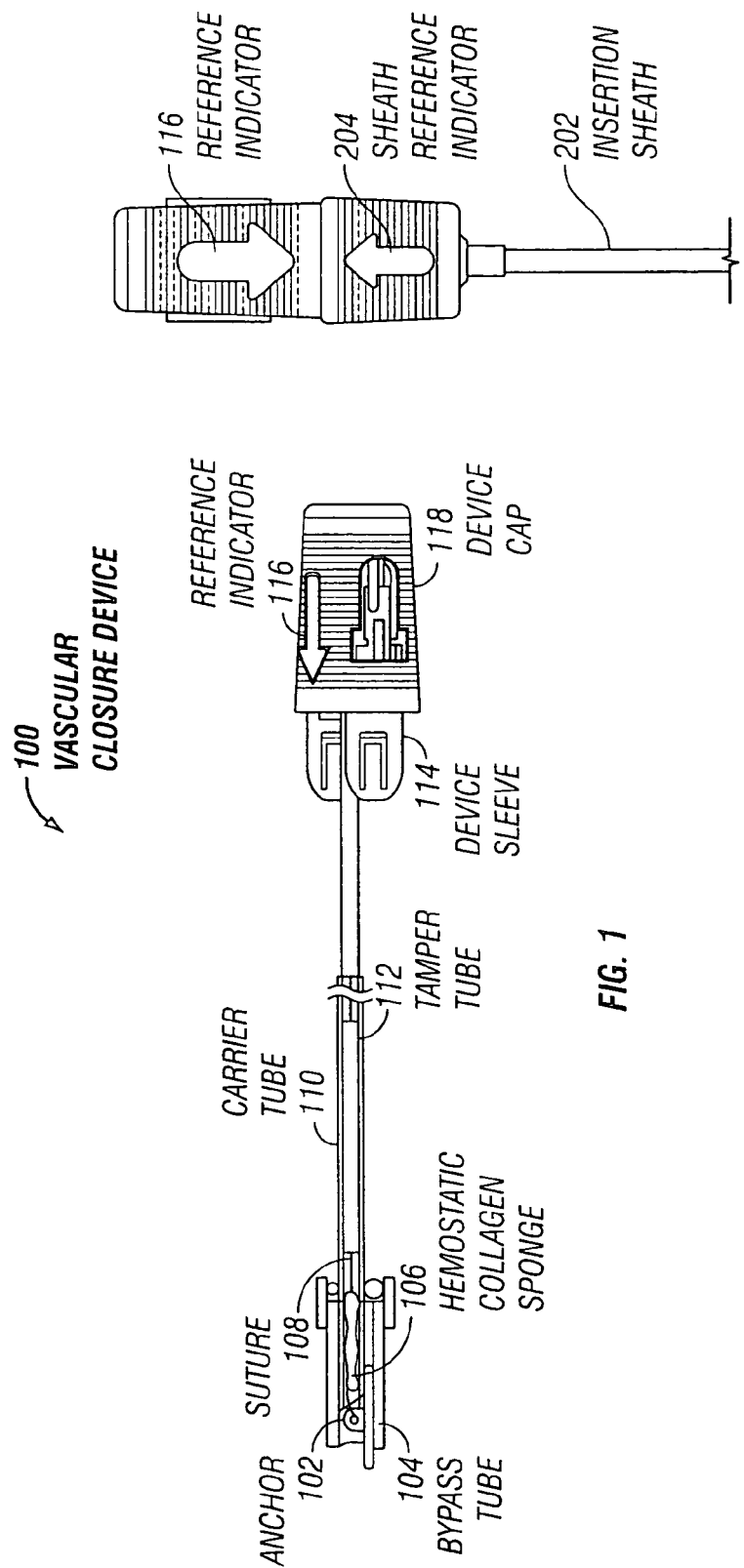

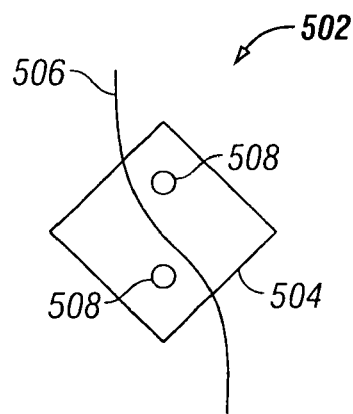
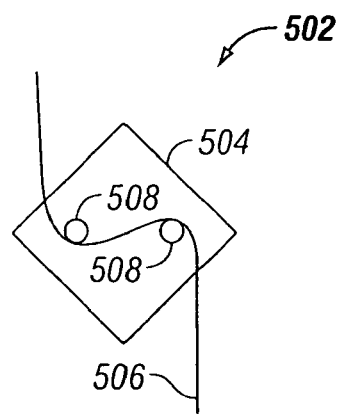
*FIG. 5A*　　　　　　　　*FIG. 5B*
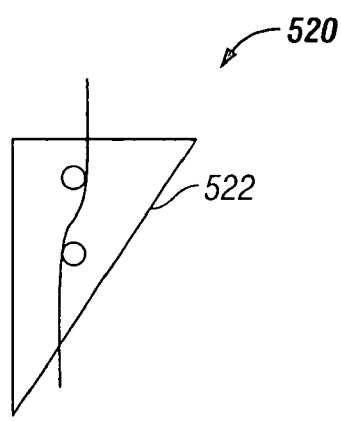
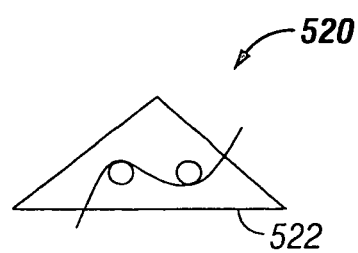
*FIG. 5C*　　　　　　　　*FIG. 5D*
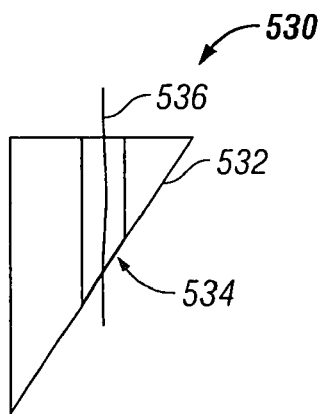
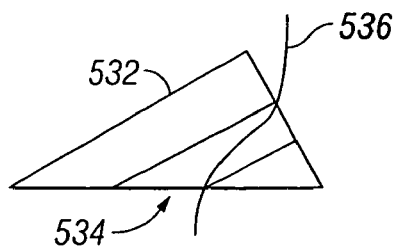
*FIG. 5E*　　　　　　　　*FIG. 5F*

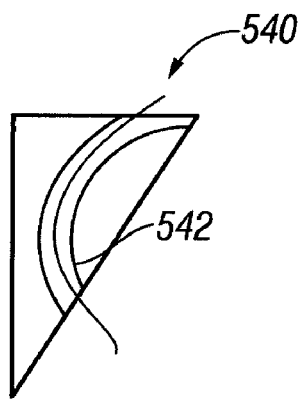
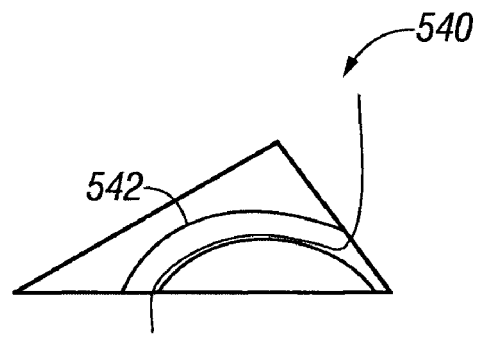
FIG. 5G
FIG. 5H
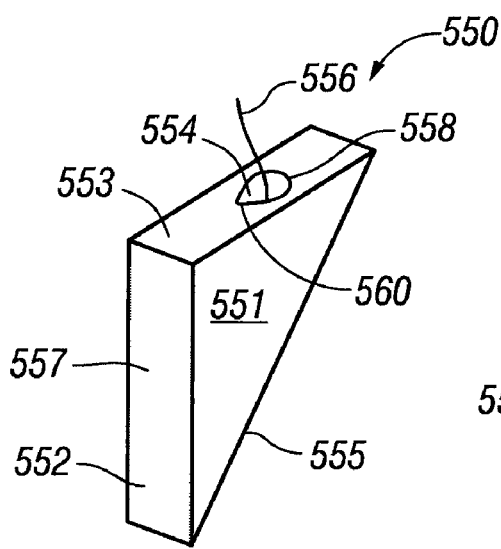
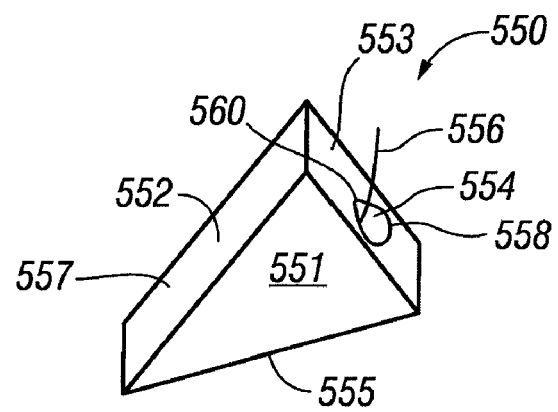
FIG. 5I
FIG. 5J

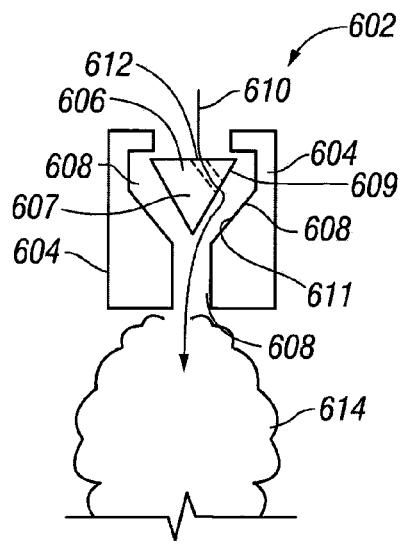
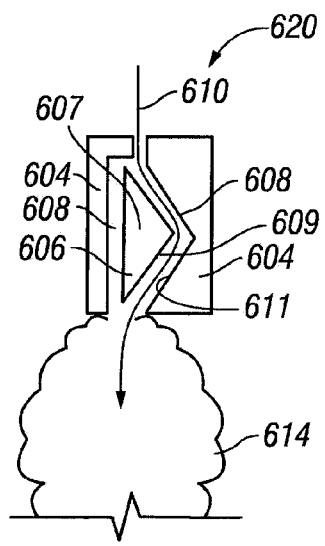
FIG. 6A    FIG. 6B
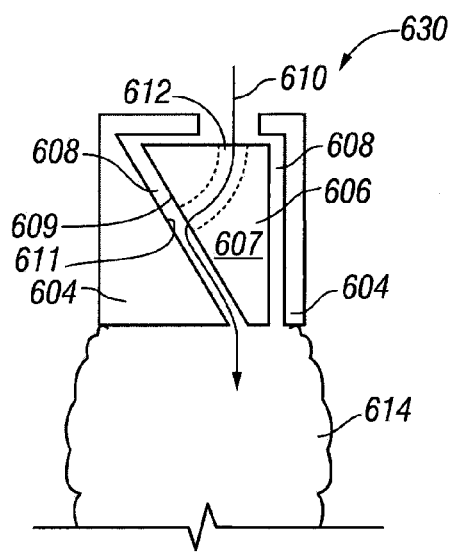
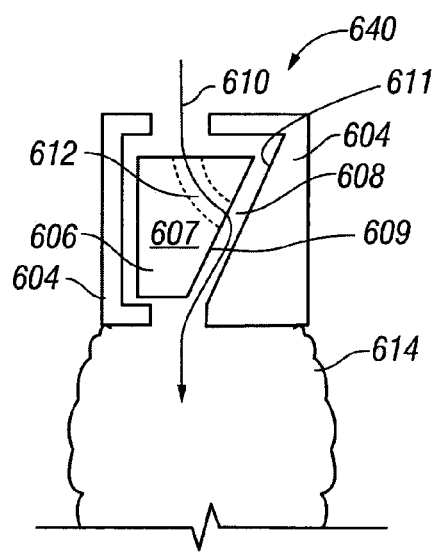
FIG. 6C    FIG. 6D

AUTOMATIC SUTURE LOCKING DEVICE

FIELD OF THE INVENTION

The present invention relates to a vascular closure devices and, more particularly, to a vascular closure device having an automatic suture locking device.

BACKGROUND OF THE INVENTION

Many surgical procedures today require entry into an arterial vessel and placement of devices using catheters or insertion sheaths. After the procedure, the arterial puncture or opening must be closed. Vascular closure procedures and devices are generally known in the art, but a brief background will be provided herein. FIG. 1 shows a conventional vascular closure device 100 useful in closing arterial punctures. Device 100 may include an anchor 102, a bypass tube 104, a hemostatic collagen sponge 106, a suture 108, a carrier tube 110, a tamper tube 112, a device sleeve 114, a reference indicator 116, and a device cap 118.

To use device 100, an insertion sheath 202 or catheter (see FIG. 2) is placed such that a tip of the insertion sheath or catheter is just beyond the arterial puncture. Any tools or devices delivered via the insertion sheath, such as, guide wires, dilators, catheters, stents, or the like, are removed. Vascular closure device 100 is delivered to the puncture site by sliding device 100 through insertion sheath 202 until reference indicator 116 lines up with an insertion sheath reference indicator 204. After lining up the reference indicators 116 and 204, the doctor begins removing vascular closure device 100 by pulling device cap 118 until slight resistance to movement is felt. When resistance is felt, anchor 102 has deployed and is flush with a tip 302 of insertion sheath 202. Of course, other deployment indications are possible.

Once the doctor has deployed anchor 102, insertion sheath 202 and vascular closure device 100 are pulled away from the puncture location leaving anchor 102, hemostatic collagen sponge 106, and suture 108 in place closing the vascular puncture. Conventionally, a doctor ties anchor 102, collagen 106, and suture 108 using a slipknot (not specifically shown but generally know in the art.) Along with other problems, the slipknot can be difficult for the doctor to deploy and can be difficult to manufacture. Thus, it would be desirable to develop an automatic suture locking device useful with vascular closure devices.

SUMMARY OF THE INVENTION

To attain the advantages and in accordance with the purpose of the invention, as embodied and broadly described herein, an automatic suture locking assembly is provided. The suture locking assembly generally comprises a housing and a locking mechanism. The locking mechanism has locked and non-locked positions. In the locked position, a suture pathway through the mechanism should be sufficiently tortuous to prevent free suture movement.

The foregoing and other features, utilities and advantages of the invention will be apparent from the following more particular description of a preferred embodiment of the invention as illustrated in the accompanying drawings.

BRIEF DESCRIPTION OF THE DRAWING

The above and other objects and advantages of the present invention will be apparent upon consideration of the following detailed description, taken in conjunction with the accompanying drawings, in which like reference characters refer to like parts throughout, and in which:

FIG. 1 is a cross-sectional view of a conventional vascular closure device;

FIG. 2 is a perspective view of a conventional vascular closure device inserted in a conventional insertion sheath;

FIGS. 5A-5J are cross-sectional views of automatic locking devices illustrative of the present invention;

FIGS. 6A-6D are cross-sectional views of automatic locking devices illustrative of the present invention.

DETAILED DESCRIPTION

Figure 3:
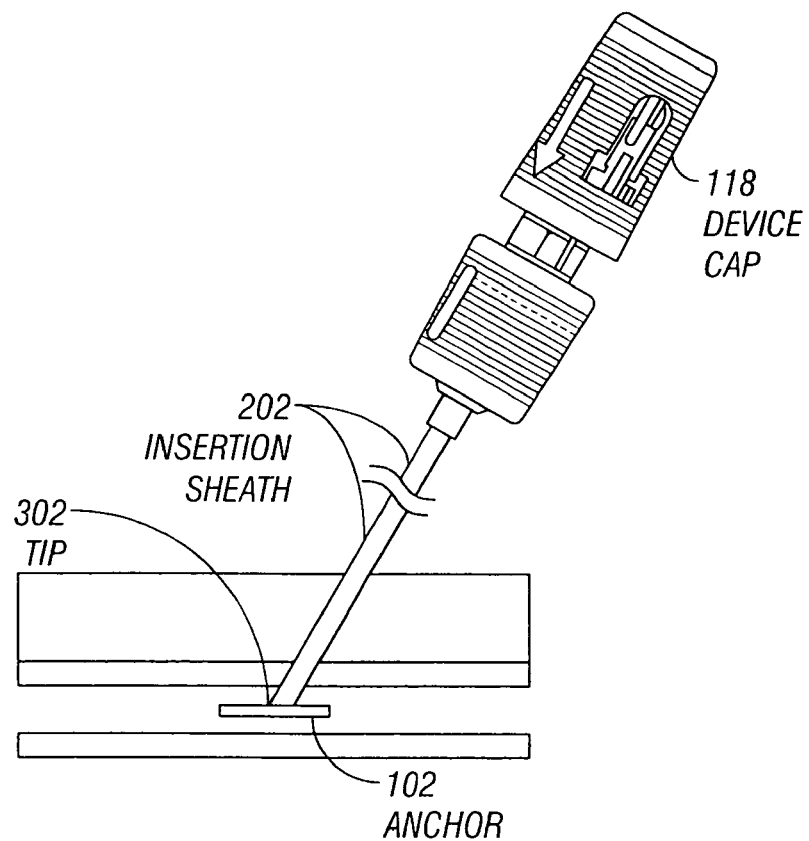
FIG. 3 is a view of a conventional vascular closure device with an anchor deployed in a patient.
Figure 4:
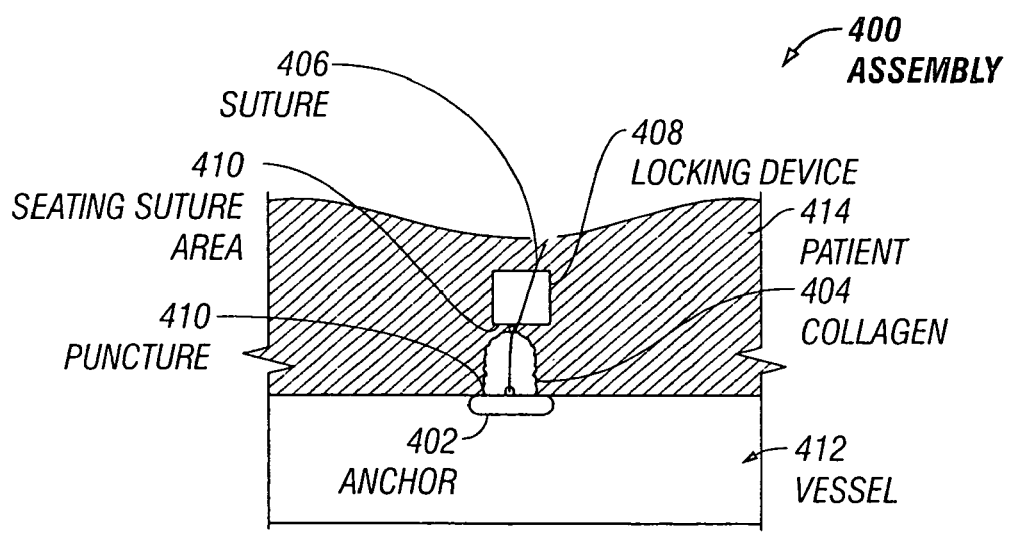
FIG. 4 is a cross-sectional view of a vascular closure assembly consistent with the present invention.

The present invention will now be described with reference to FIGS. 4-7C. Referring to FIG. 4, an assembly 400 consistent with the present invention is shown. Assembly 400 includes an anchor 402, a collagen 404, a suture 406, and an automatic locking device 408. Assembly 400 is shown deployed to close a puncture 410 in a vessel 412 of a patient 414. Largely, deployment of assembly 400 is similar to conventional vascular closure device 100 described above and will not be further explained here. While the present invention is described with reference to vascular closure devices, one of skill in the art will recognize on reading the disclosure that the present invention is useful for locking sutures in other surgical applications.

Once deployed and placed, instead of using a slip not to secure assembly 400, automatic locking device 408 is used. Automatic locking device 408 can be any number of types that will be explained further below. One advantage of locking device 408 is that it may have sufficient seating surface area 410 to inhibit locking device 408 from pushing to far into collagen 404. Further, while a doctor could manually move the locking device from a non-locked to a locked position, the locking could be accomplished automatically by, for example, using the pressures exhibited by the collagen when it expands, preloading the device, using a predefined tension on the suture, or the like.

Automatic locking device 408 can encompass many variations, some of which will be explained further below. These examples should be considered exemplary and in a non-limiting sense. Generally, the embodiments described below relate to rotating automatic locking devices 500 (FIGS. 5A-5J), sliding automatic locking devices 600 (FIGS. 6), and snap-lock automatic locking devices 700 (FIGS. 7). Automatic locking device, as well as other part, could be made from bio-resorbable polymers, such as, for example, PGA.

Rotating Automatic Locking Devices

FIGS. 5A to 5J show several embodiments of rotating automatic locking device 500. FIGS. 5A and 5B show a rotating automatic locking device 502. Device 502 has a square housing 504, a suture 506 running through housing 504, and cantilevered locking posts 508. FIG. 5A shows device 502 in a deployment state. In the deployment state, suture 506 runs through housing 504 and around locking posts 508 relatively easily.

Device 502 is rotated after deployment to locked status shown by FIG. 5B. As seen, rotating device 502 causes suture 506 to be in contact with relatively more surface area on locking posts 508. The increased friction due to the increased surface area locks suture 506 in place. Resistance could be further increased if at least one of the locking posts 508 have one or more ridges, grooves, notches, channels, or textured surfaces to increase frictional resistance.

Rotating device 502 from the deployment to locked status could be done manually by a practitioner or automatically by, for example, pressure from the expanding collagen 404. In particular, during deployment, rotating device 502 would be subject to rotating pressure from the tamper tube (not specifically shown in FIG. 4, 5A, or 5B, but generally known in the art) and equal but opposite rotating pressure from collagen 404. After deployment, the tamper tube is removed and collagen 404 applies a rotating force. In FIGS. 5A-5F, for example, device 502 is shown with a 90 degree rotation, but more or less rotation could be user as a matter of design choice. Generally, the rotation needs to be sufficient such that the suture locks after rotation is complete. In other words, as shown in FIGS. 5A-5B, suture 506 must travel a sufficiently tortuous pathway around posts 508 such that the suture 506 does not move.

FIGS. 5C and 5D show an alternative shaped rotational automatic locking devices 520. Device 520 is similar to device 502 but has a triangular housing 522 instead of a square housing. FIGS. 5E to 5H show still other embodiments of rotational automatic locking devices 530 and 540. FIGS. 5E and 5F show the deployed and locked position respectively of device 530. Device 530 also has a triangular housing 532, but it has a tube 534 or cylinder (which could be circular, square, rectangular, elliptical, triangular or the like) passing through the center instead of locking posts. A suture 536 can run through freely in the deployed position (FIG. 5E), but in the locked position (FIG. 5F) suture 536 is pinched and inhibited from movement, which locks it in place. Device 540 shows that a tube 542 can be curved.

FIGS. 5A to 5H identify several embodiments of rotational automatic locking device consistent with the present invention, but should be deemed as exemplary and not limiting. In particular, rotational automatic locks could be of most shapes or configurations, such as, for example, rectangular, trapezoidal, triangular, square, circular, elliptical, spherical, conical, or the like. At least FIGS. 5I and 5J illustrate a generally wedge shaped locking device having at least one triangle shaped side 551 and multiple planar trapezoid faces 553, 555, 557. Similarly, the lock is provided by an increase in friction that can be provided by many styles of design, such as wrapping the suture about locking posts or dragging the suture along the wall of a tube or cylinder.

FIG. 5I shows another embodiment of a rotational automatic locking device 550. Device 550 has a triangular housing 552, a tube 554 running through housing 552, and a suture 556. In this case, tube 554 (or suture pathway) has a rounded side 558 and a notched side 560 forming a tear drop shape. As shown in FIG. 5I, in the deployed state, suture 556 passes through rounded side 558 or tube 554. As shown in the locked state, however, device 550 has rotated and suture 556 passes through the notched side 560 of tube 554. Passing through notch side 560 locks suture 556 in place. To facilitate the locking of suture 556, notch side 560 could be textured, grooved, ribbed, or the like to increase resistance.

While the tear drop shape of tube 554 is somewhat arbitrary, it highlights the wide pass through portion of tube 554 and the narrow lock portion of tube 554. Other designs would work equally well, such as a triangular design, a circular design with a channel, or the like.

Sliding, Locking Device

Referring now to FIGS. 6A to 6D, sliding locking devices are shown. Referring first to FIG. 6A, a sliding, locking device 602 comprises an outer housing assembly 604, an inner housing assembly 606, at least one gap 608 between the outer housing assembly 604 and inner housing 606, and a suture 610. Suture 610 resides in the at least one gap 608, but could also reside in a channel 612 (shown in phantom) in inner housing 606. During device deployment, tamping forces and tension on suture 610 cause suture 610 to engage inner housing assembly 606 and lift inner housing. Once deployed, tamping forces are removed and tension on suture 610 is no longer sufficient to lift inner housing assembly 606. Because inner housing assembly 606 is no longer being lifted, it drops and mates with housing assembly 604, effectively clamping and locking suture 610. A collagen 614 expands and provides additional seating force between outer housing assembly 604 and inner housing assembly 606. FIGS. 6B to 6D show alternative embodiments of slide, locking assembly 620, 630, and 640. The inner housing assemblies 606 of the locking assemblies 602, 620, 630, 640 each include a wedge shaped portion 607 that is generally triangular shaped. The wedge shaped portion 607 includes a surface 609 that faces a surface 611 of the outer housing assembly 604. These embodiments should be deemed exemplary of locking mechanisms that have bodies that slide into a fitted arrangement to lock a suture.

Snap Lock Device

Figure 7A:
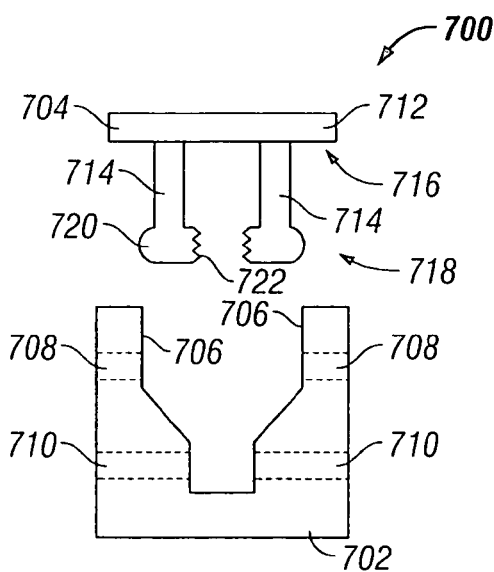
FIGS. 7A-C are cross-sectional views of automatic locking devices illustrative of the present invention.

A snap lock device will be explained with reference to FIG. 7A to FIG. 7C. FIG. 7A shows a snap lock device 700 comprises an external housing 702 and a locking device 704. External housing 702 has sidewalls 706, deploying position holes 708, which could be detents, and locking position holes 710, which could be detents. Sidewalls 706 angle inwards between holes 708 and holes 710. Locking device 704 comprises extension mount 712 and two extensions 714, although more or less extensions are possible. Extensions 714 have a proximate end 716 connected to extension mount 712 and a distal end 718. Distal end 718 comprises a tab 720 and a mating surface 722.

When device 700 is in the deploy mode, tabs 720 are engaged with deploying position holes 708. In the deploying position, a suture (not shown) would freely run through the device 700. To lock the device 700, locking device 704 would move towards external housing 702. Tabs 720 would disengage from holes 708. Extensions 714 would move inward toward each other closing a gap between opposed mating surfaces 722. In the locked position, tabs 720 would engage locking position holes 710 and opposed mating surfaces would clamp the suture, locking it in place. Optionally, when locked, extension mount 712 could engage external housing 702.

Because extensions 714 may be squeezed, as in this example, when in the locking position, they have a tendency to try and separate, which would tend to push locking device 704 away from housing 702. Thus, tabs 720 engaging locking position holes 710 inhibit extensions 714 from opening device 700.

Figure 7B:
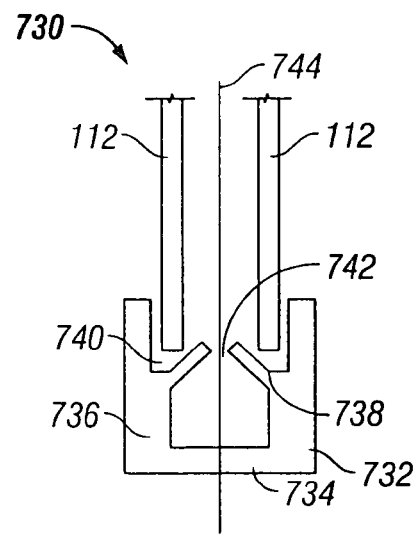
Figure 7C:
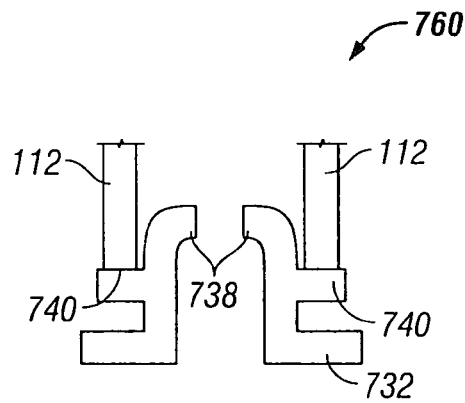

FIG. 7B shows an alternative snap-lock device 730. Device 730 has a housing 732. Housing 732 comprises a base 734 and flexible sidewalls 736. Extending inward from flexible sidewalls 736 is at least one lock tab 738. Flexible sidewalls 736 experience a compressive force tending to collapse sidewalls 736 inwardly. Flexible sidewalls 736 could be entirely made of a flexible material, such as a high density plastic, or only a portion need be flexible.

A junction 740 is formed by lock tab 738 and flexible sidewall 736. In the deploying position, an end of tamper tube 112 fits in junction 740. Tamper tube 112 resists the compressive force on flexible sidewall 736 such that lock tab 738 does not close off gap 742 through which a suture 744 runs. Once the assembly has been tampered, the lock is formed by removing tamper tube 112. When tamper tube 112 is removed, the compressive force is no longer resisted and flexible sidewalls 736 collapse inward causing lock tab 738 to close the gap 742 and lock suture 744 in place. FIG. 7C shows a similar device 760, but junction 740 is formed by outcrops from housing 732

While the invention has been particularly shown and described with reference to embodiments thereof, it will be understood by those skilled in the art that various other changes in the form and details may be made without departing from the spirit and scope of the invention.

I claim:

1. A vascular closure assembly, comprising:
    an anchor;
    a collagen;
    a suture coupled to the anchor and extending through the collagen;
    a suture locking mechanism comprising a housing and at least first and second locking posts extending cantilevered from the housing;
    the suture locking mechanism being rotatable between a non-locked position and a locked position;
    wherein the suture is capable of movement when the suture locking mechanism is in the non-locked position and the suture at least partially wraps around the first and second locking posts and is relatively incapable of movement when the suture locking mechanism is in the locked position;
    wherein rotating movement of the suture locking mechanism is configured to occur upon deployment of the anchor and the collagen.

2. The assembly according to claim 1, wherein the housing includes a wedge-shaped portion.

3. The assembly according to claim 2, wherein the wedge shaped portion includes an acute angled portion.

4. The assembly according to claim 2, wherein the wedge shaped portion includes an obtuse angled portion.

5. The assembly according to claim 1, wherein the rotating movement is caused by expansion of the collagen.

6. A vascular closure device, comprising:
    an anchor;
    a collagen;
    a locking device; and
    a suture coupled to the anchor and extending through the collagen and the locking device, wherein the locking device comprises:
        a housing; and
        at least two cantilevered locking posts extending from the housing;
        wherein the locking device being rotatable between a first orientation and a second orientation, the first orientation providing the suture with a relatively non-tortuous path defined for the suture through the locking device, and
        the second orientation providing the suture with a relatively tortuous path defined at least in part between the at least two locking posts;
        wherein rotating movement of the locking device is configured occur upon deployment of the anchor and the collagen.

7. The closure device according to claim 6, wherein the locking device includes an obtuse angled portion.

8. The closure device according to claim 6, wherein the locking device includes at least one of a textured surface, a ribbed surface, a grooved surface, a notched surface, and a channeled surface to increase the frictional resistance.

9. A vascular closure device, comprising:
    an anchor;
    a collagen;
    a suture; and
    a suture locking assembly, the suture locking assembly including a housing and at least two cantilevered locking posts extending from the housing;
    wherein the suture is coupled to the anchor and extends through the collagen and the suture locking assembly in a space defined at least in part between the at least two locking posts, the suture locking assembly being rotatable between unlocked and locked positions;
    wherein rotating movement of the suture locking assembly is configured occur upon deployment of the anchor and the collagen.

10. The vascular closure device according to claim 9 wherein in the unlocked position a pathway for the suture is relatively non-tortuous and in the locked position the pathway for the suture is relatively tortuous.

11. A vascular closure assembly, comprising:
    an anchor;
    a collagen;
    a suture coupled to the anchor and extending through the collagen;
    a locking element comprising a housing and at least first and second cantilevered locking posts extending from the housing;
    the locking element being rotatable between a first orientation and a second orientation;
    in the first orientation, the locking element provides a non-tortuous pathway for the suture that is defined at least in part between the first and second locking posts such that the suture can move relative to the housing; and
    in the second orientation, the locking element provides a tortuous pathway for the suture that is defined at least in part between the first and second locking posts such that the suture is relatively immobile relative to the housing;
    wherein rotating movement of the locking element is configured to occur upon deployment of the anchor and the collagen.

12. The vascular closure assembly according to claim 11, wherein the locking element comprises a bio-resorbable material.

13. A vascular closure assembly, comprising:
    an anchor;
    a collagen;
    a suture coupled to the anchor and extending through the collagen;
    a locking device comprising a housing and at least two cantilevered locking posts extending from the housing, the locking device being rotatable between a first position and a second position;
    in the first position, the suture can move relative to the locking device; and
    in the second position, the suture is relatively immobile relative to the locking device;
    wherein rotating movement of the locking device is configured to occur upon deployment of the anchor and the collagen.

14. The vascular closure assembly according to claim 13, wherein the locking device comprises a bio-resorbable material.

* * * * *